United States Patent [19]
Holland et al.

[11] Patent Number: 5,209,233
[45] Date of Patent: May 11, 1993

[54] TEMPERATURE SENSING AND CONTROL SYSTEM FOR CARDIAC MONITORING ELECTRODES

[75] Inventors: G. Neil Holland, Chagrin Falls; Douglas M. Blakeley, Euclid; Theodore J. Reisker, Lyndhurst; David A. Molyneaux, Willowick, all of Ohio

[73] Assignee: Picker International, Inc., Highland Heights, Ohio

[21] Appl. No.: 653,628

[22] Filed: Feb. 11, 1991

Related U.S. Application Data

[63] Continuation-in-part of Ser. No. 439,855, Nov. 21, 1989, Pat. No. 4,991,587, which is a continuation-in-part of Ser. No. 98,546, Sep. 18, 1987, abandoned, which is a continuation of Ser. No. 764,440, Aug. 9, 1985, Pat. No. 4,694,837.

[51] Int. Cl.$^5$ ............................................. A61B 5/055
[52] U.S. Cl. ................... 128/653.2; 128/671; 128/696; 128/901
[58] Field of Search ............... 128/653.2, 653.5, 696, 128/670, 671, 901, 908, 653.1

[56] References Cited

U.S. PATENT DOCUMENTS

| | | | |
|---|---|---|---|
| 3,910,257 | 10/1975 | Fletcher et al. | 128/908 |
| 4,095,588 | 6/1978 | Goldman et al. | |
| 4,308,870 | 1/1982 | Arkans | |
| 4,545,384 | 10/1985 | Kawachi | 128/653 |
| 4,763,075 | 8/1988 | Weigert | 324/318 |
| 4,951,672 | 8/1990 | Buchwald et al. | 128/653.5 |

FOREIGN PATENT DOCUMENTS

| | | | |
|---|---|---|---|
| 0132785 | 2/1985 | European Pat. Off. | 128/653.2 |
| 0343858 | 11/1989 | European Pat. Off. | |
| 3430625 | 2/1986 | Fed. Rep. of Germany | 128/653.2 |

OTHER PUBLICATIONS

Cardiac Response to Pulsed Magnetic Fields with Regard to Safety in NMR Imaging; McRobbie, et al.; Phys. Med. Biol., 1985, vol. 30, No. 7, 695–702.

Primary Examiner—Ruth S. Smith
Attorney, Agent, or Firm—Fay, Sharpe, Beall, Fagan, Minnich & McKee

[57] ABSTRACT

A cardiac electrode (40) has a plug (48) which is frictionally received in a socket (50) of an electrical lead (56). An impedance (54) is connected in series between the electrical lead and the socket to pass ECG signals substantially unattenuated and for blocking radio frequency signals induced in the lead from reaching the socket and the electrode and heating the electrode to a sufficient temperature to burn the patient. The impedance includes an LC circuit (66, 68) which freely passes low frequency signals, such as cardiac signals, but which is tuned to resonance at radio frequencies, particularly at the frequency of resonance excitation and manipulation pulses of a magnetic resonance imager (A). Alternately, the impedance may include a resistive element for blocking the induced currents. A temperature sensor (60) is mounted in intimate contact with an electrically and thermally conductive socket portion (52) to sense the temperature of the electrode, indirectly. A temperature sensor lead (62), the cardiac lead (56), and a respiratory or other anatomical condition sensor are connected with a multiplexing means (140) which cyclically connects the output signals thereof with an analog to digital converter (142). The digital signals are converted to digital optical signals (102) to be conveyed along a light path (104) out of the examination region. The bits of the received digital signal are sorted (144) between an R-wave detector (120), a temperature limit check (122) which checks whether the temperature of the electrode exceeds preselected limits, and a respiratory detector (132).

21 Claims, 6 Drawing Sheets

TEMPERATURE SENSING AND CONTROL SYSTEM FOR CARDIAC MONITORING ELECTRODES

This application is a continuation-in-part of U.S. application Ser. No. 439,855 filed Nov. 21, 1989, now U.S. Pat. No. 4,991,587, which in turn is a continuation-in-part of U.S. application Ser. No. 098,546, filed Sep. 18, 1987 now abandoned, which in turn is a continuation of U.S. application Ser. No. 764,440, filed Aug. 9, 1985, now U.S. Pat. No. 4,694,837.

BACKGROUND OF THE INVENTION

The present invention relates to the art of non-invasive anatomical condition examination. It finds particular application in conjunction with cardiac gated magnetic resonance imaging and will be described with particular reference thereto. However, it is to be appreciated that the invention may find application in other non-invasive examination techniques in which conductive leads extend through changing magnetic fields.

Magnetic resonance imaging sequences commonly include the application of a radio frequency pulse concurrently with a slice select magnetic field gradient pulse. A phase encode magnetic field gradient pulse encodes phase into the nuclei induced resonance by the radio frequency pulse. Another radio frequency pulse is applied to invert the magnetic resonance and cause a magnetic resonance echo. The echo is read in the presence of a read magnetic field gradient pulse. Dephasing magnetic field gradient pulses in the slice select and read direction are commonly applied with an opposite polarity between the slice select and read gradient pulses. This sequence is repeated a multiplicity of times, each time with a different amplitude phase encode magnetic field gradient in order to generate a corresponding multiplicity of differently phase encoded views.

Anatomical movement, such as cardiac and respiratory motion, tends to degrade the resultant images. The amount of degradation is related to the amount or magnitude of physiological displacement from view to view, the rate of movement, and the like. Various anatomical condition monitors have been utilized to control the collection, processing, or use of magnetic resonance and other non-invasive imaging data in accordance with physiological motion. See for example, U.S. Pat. Nos. 4,763,075 to Weigert and 4,545,384 to Kawachi.

A patient's cardiac cycle is normally sensed with electro-cardiographic electrodes mounted to the patient's skin and connected by electrically conductive leads to processing circuitry. The electrodes commonly include a silver halide electrically conductive film which is covered by a thin layer of electrically conductive gel impregnated foam to assure good electrical connection with the patient's skin. An adhesive pad surrounds the electrode to hold it firmly and securely to a selected portion of the patient's skin. The silver halide film is connected with a metallic detent which is snap fit into a corresponding conductive clip or socket at the end of each lead.

On occasion, patients complain of a burning sensation under the cardiac electrodes during a magnetic resonance examination. When the electro-cardiographic electrode pads are removed, red marks are sometimes visible on the patient's skin. Although these marks were originally attributed to an allergic reaction to the electrically conductive gel or irritation from the adhesives, there is now evidence that patients have actually been burned by the pads. See Kanal, et al., *Radiology* 176:593-606, 1990.

The present invention contemplates a new and improved construction for the prevention of localized heating under cardiac electrodes and a method for the sensing of skin temperature in order to effect monitoring of the patient's skin temperature.

SUMMARY OF THE INVENTION

In accordance with one aspect of the present invention, a magnetic resonance imaging system is provided for receiving a patient in an imaging region. Electrode pads for interconnection to a patient are connected by electrical leads to an anatomical condition monitoring means. A temperature monitoring means is mounted in association with the pads to monitor the temperature thereof.

In accordance with a more limited aspect of the present invention, each lead includes a conductive clip or socket which releasably engages a contact portion or plug of an associated pad. The temperature sensing means is mounted in the clip to sense the temperature of the clip directly and the temperature of the electrode pad indirectly.

In accordance with a second aspect of the present invention, a magnetic resonance imaging system is provided for receiving a patient in an imaging region. Electrode pads for interconnection to a patient are connected by electrical leads to an anatomical condition monitoring means. An electrical impedance is mounted in each lead adjacent the associated pad for inhibiting currents induced in the electrical leads by the radio frequency pulses or magnetic field gradient pulses from reaching the electrodes.

In accordance with a more limited aspect of the present invention, the impedance is one of a resistive load, a parallel resonant LC circuit that blocks the passage of signals of a frequency near the frequency of the radio frequency pulses and passes signals of a frequency near the frequency of the cardiac pulses, a series resonant circuit which attenuates radio frequency signals of higher frequencies without degrading an ECG waveform, and a combination of two or more of resistive, parallel LC and series LC circuits.

One advantage of the present invention is that it protects a patient from burns.

Another advantage of the present invention is that it provides accurate, recordable information regarding electrode temperature.

Another advantage of the present invention is that it inhibits localized heating by limiting the flow of induced currents in electrical leads.

Still further advantages of the present invention will become apparent to those of ordinary skill in the art upon reading and understanding the followed detailed description.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
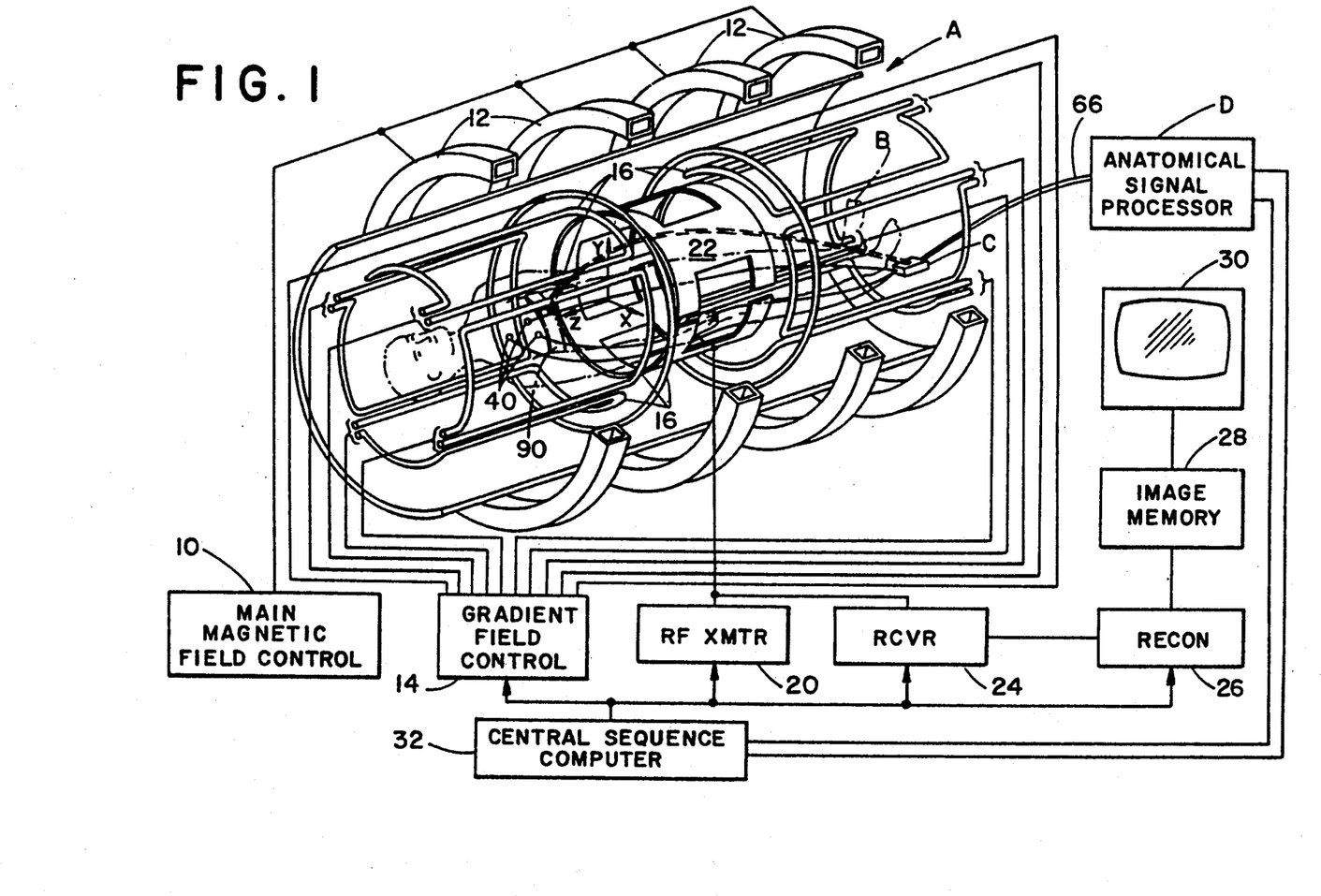
FIG. 1 is a diagrammatic illustration of a magnetic resonance imaging apparatus in accordance with the present invention.

With reference to FIG. 1, a non-invasive examination apparatus A, such as a magnetic resonance imaging apparatus, receives a subject, particularly a patient B who is to undergo a non-invasive examination. A monitoring means C is disposed adjacent the subject and interconnected with a remote condition signal processing means D. The monitoring means monitors preselected conditions, such as cardiac, respiratory, other anatomical cycles of the patient, temperature of the patient or associated equipment such as ECG electrodes, and other system or anatomical conditions. An output signal from the monitoring means C conveys monitored condition information to the processing means D. The processing means D derives monitored condition information from the received data. Optionally, the information is conveyed to the magnetic resonance imaging apparatus A for use in controlling timing of the imaging sequence, the processing of collected data, the collection or filtering of magnetic resonance data, and the like.

The magnetic resonance imaging apparatus includes a main magnetic field controller 10 which controls resistive or superconducting main magnetic field coils 12 to generate a substantially uniform magnetic field longitudinally through an imaging region. A magnetic field gradient control means 14 applies appropriate current pulses to gradient field coils 16 to create gradients across the main magnetic field. The exact nature and sequence of the gradients is determined by which of the many magnetic imaging sequences is chosen. A radio frequency transmitter 20 generates magnetic resonance excitation, inversion, and manipulation pulses which are applied to a radio frequency coil 22. The gradient and radio frequency pulse sequences are conventional in the art. A radio frequency receiver 24 receives radio frequency magnetic resonance signals from the subject in the examination region. The resonance signals may be picked up by the radio frequency coil 22 or by localized reception coils (not shown). A reconstruction means 26 utilizes a two dimensional inverse Fourier transform or other known algorithm to construct an electronic image representation from the received magnetic resonance signals. Generally, each echo or other signal is reconstructed into one view, which views are summed into an image memory 28. Completed images in the image memory may be displayed on a video display monitor 30, subject to further processing, or archived on tape or disk.

A magnetic resonance sequence control means 32 controls the timing with which the gradient field control means and the radio frequency transmitter apply gradient and radio frequency pulses in order to implement one of the conventional magnetic resonance imaging sequences. The timing or spacing between repetitions of the pulse sequence may be adjusted such that each sequence is taken within a preselected range of anatomical motion. Alternately, the radio frequency receiver 24 or the reconstruction means 26 may be controlled to discard data taken during inappropriate ranges of anatomical movement, to subject such data to heavier filtering, to replace such data with the average of adjoining views, or the like.

Figure 2:
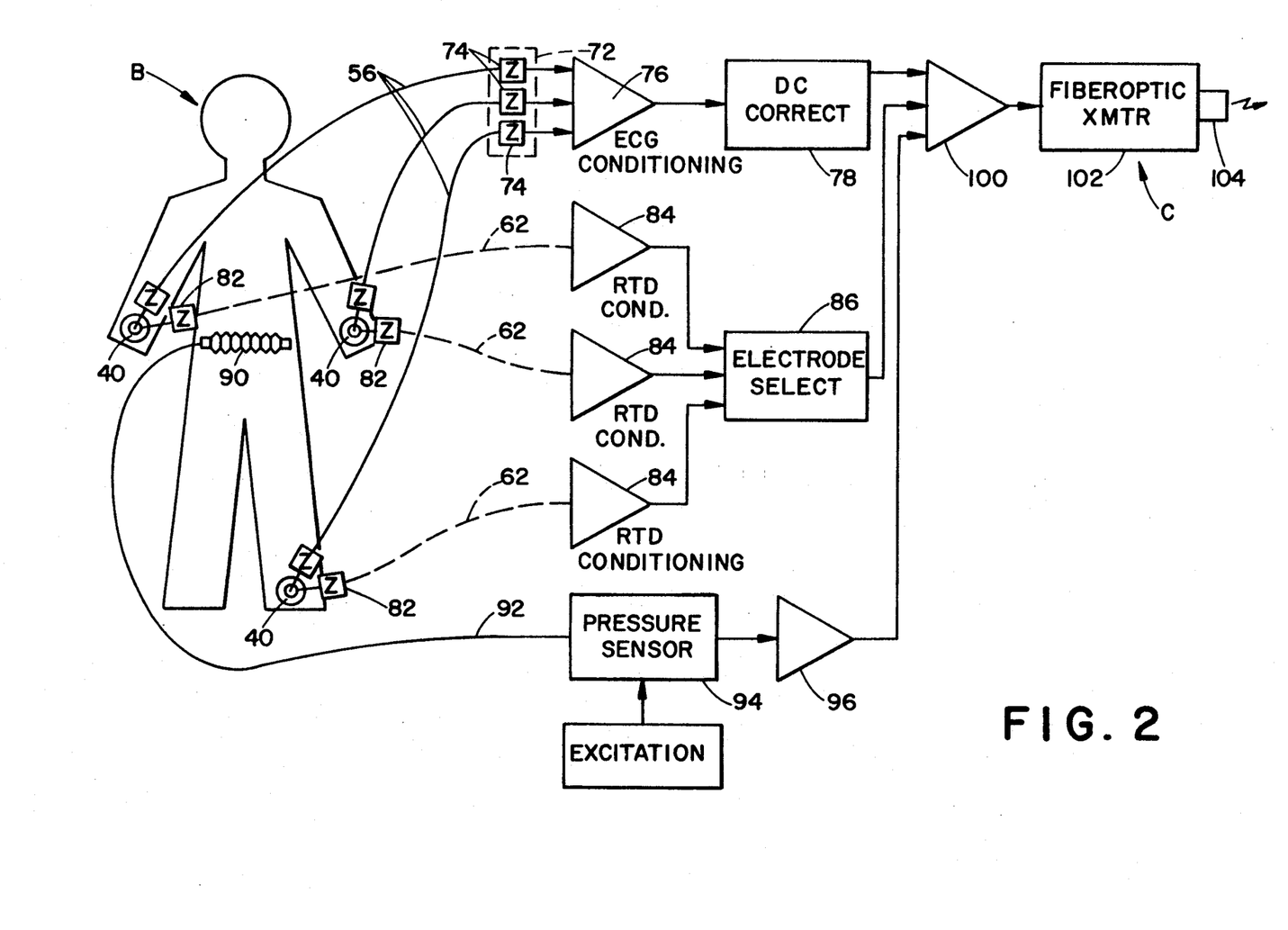
FIG. 2 is a diagrammatic illustration of the cardiac, respiratory, and electrode temperature monitoring apparatus of FIG. 1.
Figure 3:
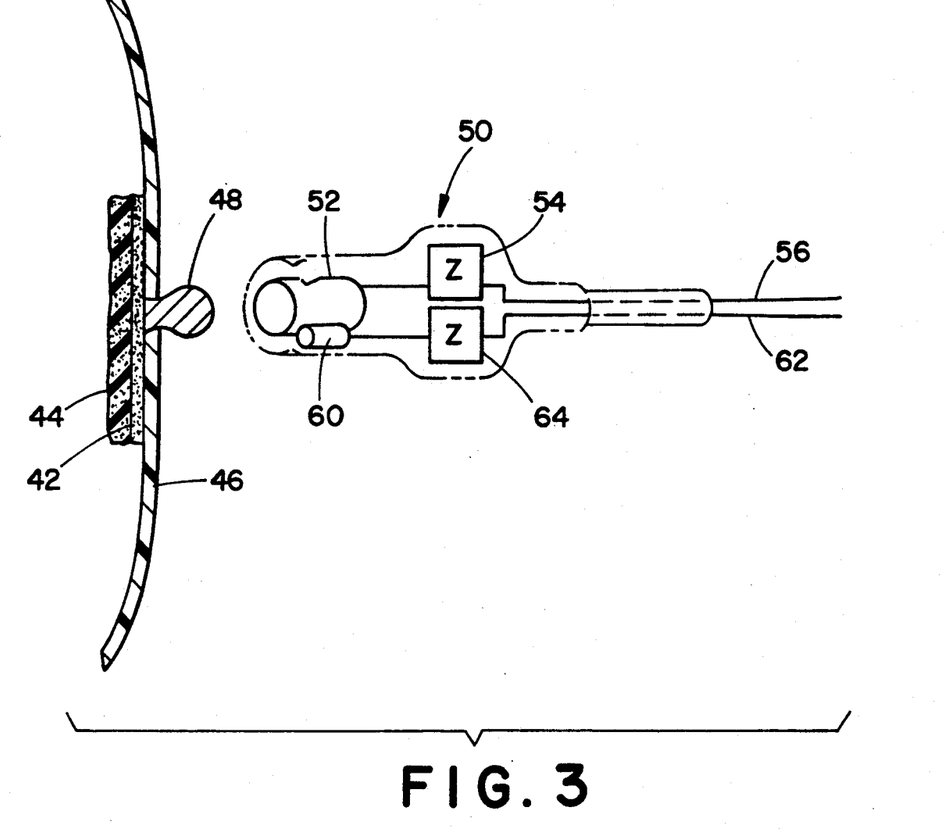
FIG. 3 illustrates an electrode, chip, temperature sensor, and induced current blocking circuit.

With reference to FIGS. 2 and 3, the patient monitor means C includes a first condition detector, in the preferred embodiment ECG electrodes 40 for monitoring the patient's cardiac cycle. Each electrode includes an electrically conductive surface or film 42 and an electrically conductive gel impregnated sponge or foam 44 for establishing electrical contact with the patient. An adhesive surfaced peripheral flange 46 secures the electrode firmly to the patient. The electrically conductive surface 42 is electrically connected with a detent or plug means 48 which is selectively snapped into and out of a connector 50.

The connector 50 includes an electrically conductive socket 52 which receives and engages the detent or plug 48. Preferably, the socket 52 has a series of electrically conductive spring members which engage and resiliently hold an enlargement on the plug member 48. The socket 52 is connected with an induced current blocking impedance 54. Cardiac signals are conveyed through the electrically conductive gel of the sponge 44, the electrically conductive surface 42, the plug 48, the socket 52, the impedance 54, and an ECG lead 56.

A temperature sensing means 60, such as a resistive temperature device (RTD) or a thermistor, monitors the temperature of the socket 52. Because the socket 52 is in intimate thermal contact with the plug 48 and the electrically conductive surface 42, the temperature sensor means 60 provides an output indicative of the temperature of the electrode 40. The temperature sensing means is connected with a temperature signal carrying lead 62. In the preferred resistive temperature device, a DC voltage is applied across the ECG lead 56 which is also connected to one end of the resistive temperature device 60 and the temperature sensor lead 62 to monitor temperature dependent changes in the resistance of the resistive temperature device.

Other temperature sensors are also contemplated. In another embodiment, the temperature sensing means 60 is a fluoroptic temperature sensor. The fluoroptic temperature sensor includes an optic fiber that has a phosphor on the end surface thereof whose fluorescence varies as a known function of temperature. In this manner, the light carried on optical fiber temperature lead 62 is indicative of socket, hence electrode, temperature.

The electrical temperature sensing device 60 is connected with the temperature output lead 62 with a second impedance means 64. The second impedance means 64 is of similar construction to the impedance means 54 to prevent currents induced in the temperature output lead 62 from reaching the socket through the resistive temperature device and cause heating of the electrode.

Figure 4:
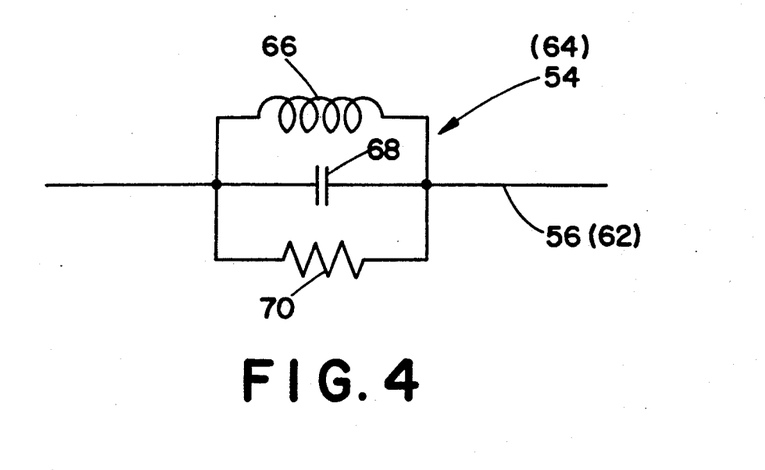
FIG. 4 illustrates one embodiment of the induced current blocking array of FIG. 2.

With reference to FIG. 4, the impedance means 54 and 64 are selected to pass cardiac and temperature signals respectively with essentially no degradation, but to block the passage of electrical currents induced in the leads 56 and 62 by the radio frequency signals applied in the magnetic resonance sequence or induced by the changing magnetic field gradients. The frequency of currents induced by the radio frequency pulses will have substantially the same frequency as the radio frequency pulses, generally in the MHz range. For a 1.5 Tesla scanner, the radio frequency pulses are commonly about 64 MHz. Because cardiac signals are typically in the 0–150 Hz range, they are readily distinguishable from the induced currents and can be selectively blocked or passed on the basis of frequency. In the embodiment of FIG. 4, an LC bandpass filter circuit including a parallel connected inductor 66 and capacitor 68 are connected in series with the electrically conductive lead 56 (62). The inductive and capacitive elements are selected such that they pass cardiac and temperature signals in the range of about 0–150 Hz substantially unattenuated, i.e. the LC circuit is substantially invisible to the cardiac signals. Yet, the components are selected to block currents induced by the radio frequency pulses of the imaging sequence in the MHz range. That is, the filter appears as a very large impedance or open circuit to the high frequency induced currents. Optionally, a resistor 70 is connected in parallel with the inductor 66 and capacitor 68 to lower the Q or quality factor of the circuit to broaden the frequency band in which the circuit appears as an open circuit or very high impedance.

With reference again to FIG. 2, a protection circuit 72 is connected in series with each lead to protect the downstream electronics from induced currents. The protection circuit 72 includes an impedance 74 in series with each electrical lead, which impedance is preferably of an analogous construction to impedances 54 and 64. An amplifier 76 adjusts the magnitude of the cardiac signals. Although the impedances 74 are selected to block radio frequency induced currents, a slew rate limiting means may be provided to remove other frequency components that are not commonly found in cardiac signals. A DC correction means 78 removes DC offset.

The electrical temperature sensor output leads 62 are connected with a protection circuit having impedances or filters 82 which are again analogous to impedances 54 and 64 for protecting upstream circuitry from currents induced in the leads 62. Amplifier means 84 adjust the magnitude of the received temperature signals. Alternately, for fiberoptic leads, no protection impedances are used. Means 84 converts the optical signals into electrical signals and adjusts the magnitude of the electrical signals. An electrode selection means 86 selects one of the temperature outputs to be communicated. In the preferred embodiment, the highest sensed temperature is selected, e.g. with a peak detector. Alternately, the temperatures of each electrode may be cyclically forwarded.

A respiratory monitor, such as an air-filled elastomeric belt 90 expands and contracts with the patient's breathing. The expansion and contraction causes corresponding changes in air pressure in a tube 92. A pressure sensor 94 converts the changes in air pressure communicated by tube 92 into electrical signals indicative of the patient's respiratory cycle. A typical pressure sensor is a balanced bridge pressure to electrical signal transducer that has a bridge circuit across which an oscillator applies a carrier signal, e.g. 2 KHz. The carrier signal modulates the respiratory signal to create an output signal in a frequency range that is readily separated from the cardiac and temperature signals. A beat pattern or amplitude variation of the modulated signal carries the encoded respiratory cycle data. An amplifier 96 amplifies the respiratory signal. Optionally, a bandpass filter may remove noise and distortion components.

Because the cardiac, temperature, and respiratory signals are all at distinctly different and identifiable frequencies, all are summed by a summing amplifier 100 to form a Composite, analog signal. The composite analog output from the summing means is converted to an output optical signal by an analog fiberoptic transmitter 102. The frequency of the light signals from the transmitter is modulated in proportion to the magnitude of the voltage of the output signal from the summing amplifier and conveyed along an optic transmission path 104, such as an optic fiber or laser beam.

Figure 5:
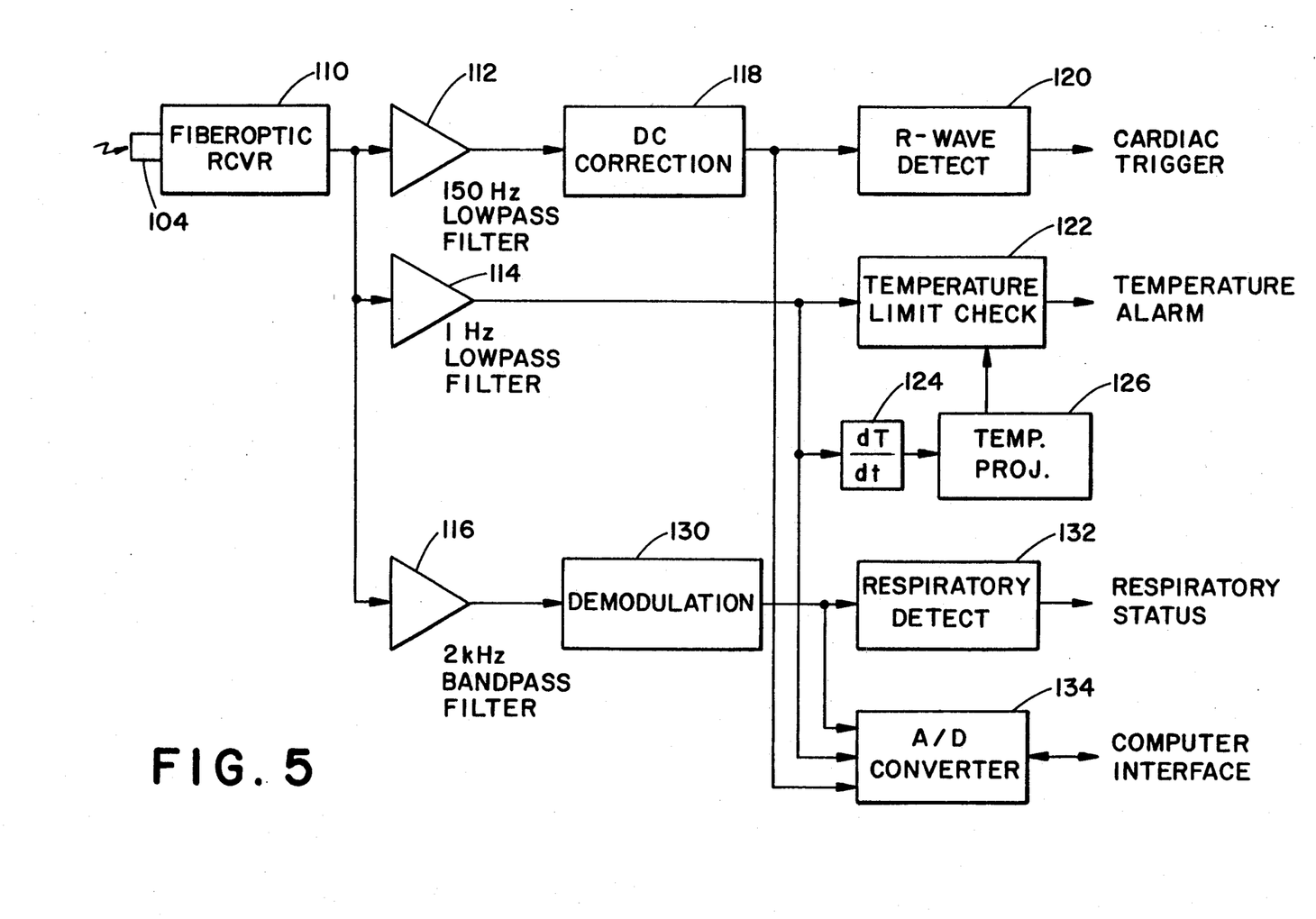
FIG. 5 is a diagrammatic illustration of a cardiac, temperature, and respiratory signal processing apparatus of FIG. 1.

With reference to FIG. 5, a fiberoptic receiver 110 receives the light cardiac, temperature, and respiratory signals and converts them to corresponding electrical signals. The electrical signals from the fiberoptic receiver 110 are conveyed to bandpass filters 112, 114, and 116. The bandpass filter 112 is a low pass filter which passes low frequency signals, e.g. signals between 10 and 150 Hz. A DC correction means 118 performs a DC correction on the signals passed by the low pass filter 112. An analog R-wave detecting means 120 detects the R-wave of these signals.

The bandpass filter 114 passes signals with a frequency below about 1 Hz, i.e. the electrode temperature signal. The temperature limit means 122 compares the temperature signal with the preselected temperature. Optionally, a temperature rate of change determining means 124 monitors the rate of change of the temperature. A temperature projecting means 126 determines the rate at which the temperature is approaching the preselected temperature limit. In response to the temperature exceeding the limit temperature or in response to the temperature approaching the limit temperature to within preselected tolerances at greater than a preselected rate, a temperature alarm is sounded. The alarm may be merely a verbal or visual warning or may be a signal to the central sequence computer 32 which terminates the scan sequence.

The bandpass filter 116 passes signals with a frequency about 2 KHz, i.e. the respiratory signals. A demodulation circuit 130 demodulates the respiratory signal from the 2 KHz carrier. A respiratory detector 132 receives the respiratory signals and provides respiratory status signals to the central sequence computer means 32. This enables the central sequence computer to trigger a scan only at appropriate phases of the respiratory and cardiac cycles and when the temperatures of the electrodes are within appropriate ranges.

The DC correction means 118, the low pass filter 114, and the demodulation means 130 are connected with an analog to digital converter 134 for digitizing the cardiac, temperature, and respiratory information for convenient computer interface.

Figure 6:
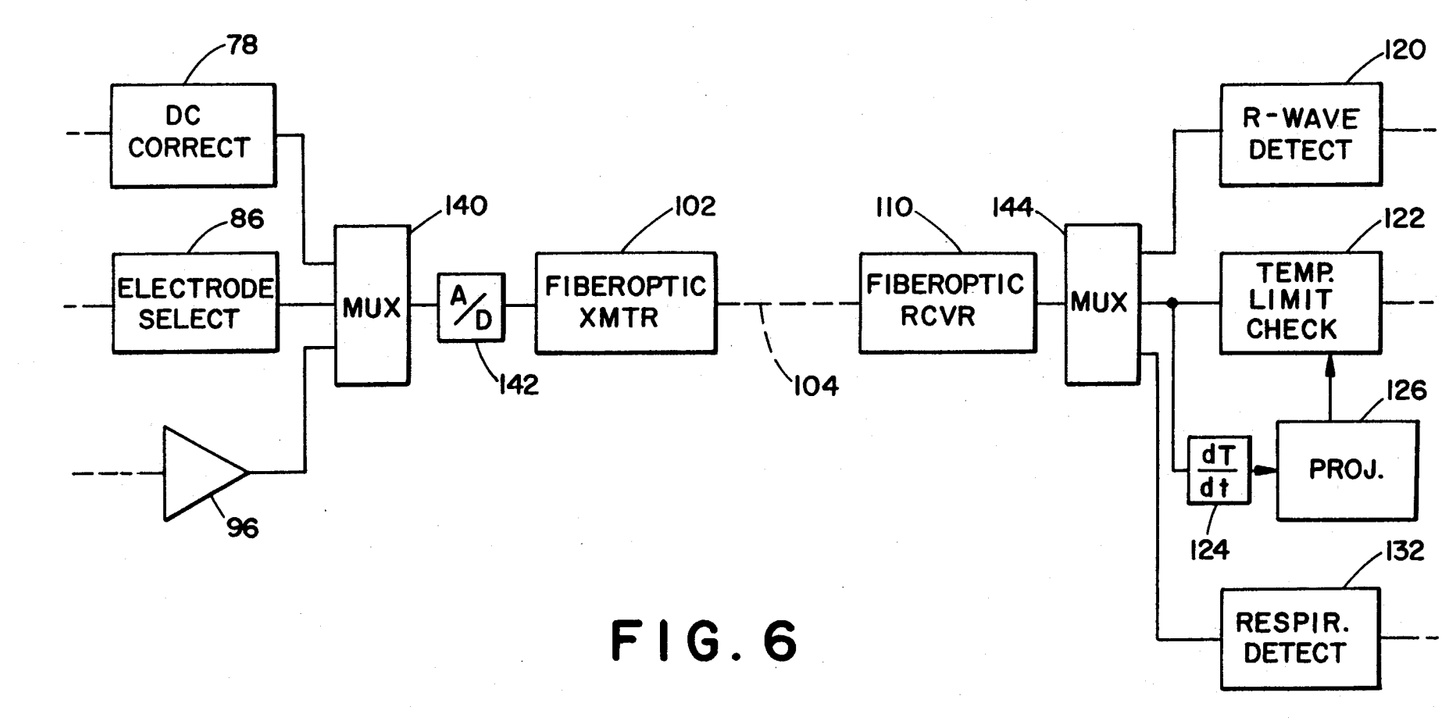
FIG. 6 is an alternate embodiment in which the cardiac, temperature, and respiratory signals are transmitted digitally along the optic path.

With reference to FIG. 6, the cardiac, temperature, respiratory, and any other monitored conditions can be encoded and transmitted digitally. The analog cardiac, temperature, respiratory, and any other monitored condition signals are communicated to a multiplexing or selecting means 140. The multiplexing means is clocked at a high frequency to connect each of the cardiac, temperature, respiratory, and other condition signals cyclically with an analog to digital convertor 142. The digital output signals are transmitted by a digital, fiber-optic transmitter 102 along the fiberoptic output cable 104. The clocking rate of the multiplexer is selected in accordance with the speed of the analog to digital convertor and the digital fiberoptic transmitter. Of course, the multiplexer or selecting means 140 need not cause the signals to be digitized in cyclic order. Rather, the more rapidly changing signals, such as the cardiac signal, may be connected more frequently with the analog to digital convertor than the slower changing signals such as the temperature and respiratory signals.

The digital optical signals on the fiberoptic transmission line 104 are received by the fiberoptic receiver 110. The digital signals are transmitted to a sorting means 144 which separates the portions of the digital signal attributable to the cardiac signal, the temperature signal, the respiratory signal, and other condition signals from each other. The cardiac signals are communicated to the R-wave detecting means 120 which issues a trigger signal to the central sequence computer 32 in response to each detected R-wave. The R-wave detecting means 126 may operate directly on the digital cardiac signal. Alternately, a digital to analog converting means may convert the cardiac signal to analog form prior to detection of the R-wave.

The sorting means 144 sends the digital temperature signal to the temperature limit checking means 122-126 which compares the received temperature signal with the preselected limits.

The sorting means 144 sends the digital respiratory signals to the respiratory detection circuit 132 that monitors the status of the respiratory cycle. Preferably, the digital respiratory signals are not modulated with a higher frequency signal eliminating the need to demodulate the signal.

Figure 7:
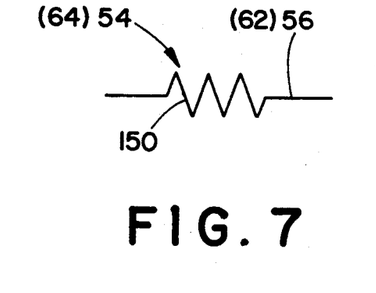
FIG. 7 is an alternate embodiment of the induced current blocking array of FIG. 4 in which the impedances are series resistors.

With reference to FIG. 7, the impedance or filter arrays 54, 64 and may include a resistor 150, e.g. a 10 K-ohm resistor, in series with the lead. The resistor shunts RF flowing from the ECG leads to the ECG electrodes. The resistor is selected to have a low capacitance and a large impedance to limit RF current flowing from the leads to the ECG electrodes.

Figure 8:
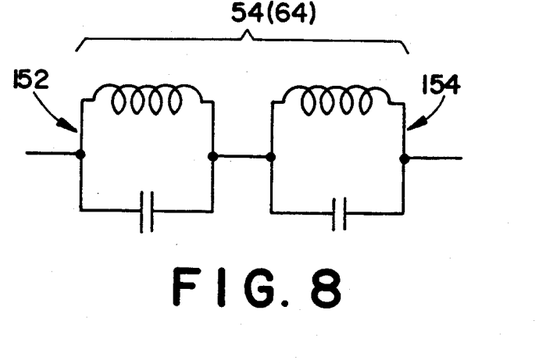
FIG. 8 is an alternate embodiment of the induced current blocking array of FIG. 4 which includes multiple, parallel resonant modes in series with the ECG leads.

With reference to FIG. 8, each of the arrays may include parallel resonance circuits with multiple resonance modes. A first LC resonance circuit 152 and a second LC resonance circuit 154 have inductors and capacitances selected to cover two or more frequencies. This enables the same leads to be used with magnetic resonance apparatus having different field strengths or operating frequencies.

Figure 9:
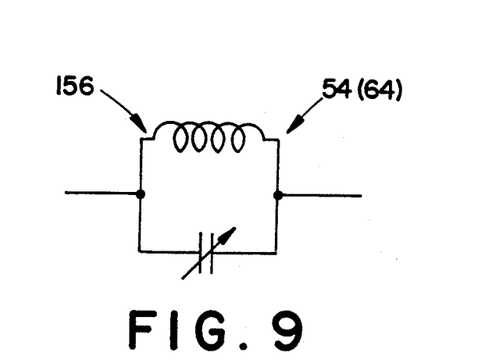
FIG. 9 is another alternate embodiment of the induced current blocking array of FIG. 4 which includes a tuneable, parallel LC circuit in series with the ECG lead.

Alternately, as shown in FIG. 9, an LC filter circuit 156 may have a variable capacitor for selectively tuning the resonance frequency. This enables the impedance to be adjusted for different field strength apparatus or the like.

Figure 10:
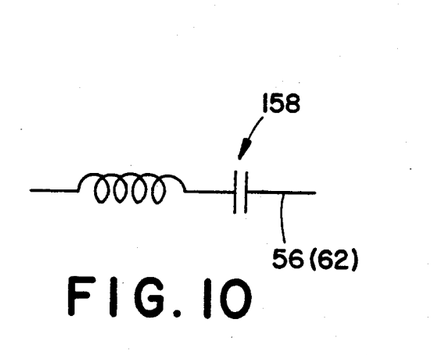
FIG. 10 is another alternate embodiment of the induced current blocking array of FIG. 4 which includes a series resonant circuit in series with the ECG lead; and, FIG. 11 is another alternate embodiment of the induced current blocking array with combined series and parallel resonant LC circuits.

With reference to FIG. 10, a series resonant LC circuit 158 has inductive and capacitive components which pass signals in the ECG frequency range but which attenuate signals of higher frequencies.

Figure 11:
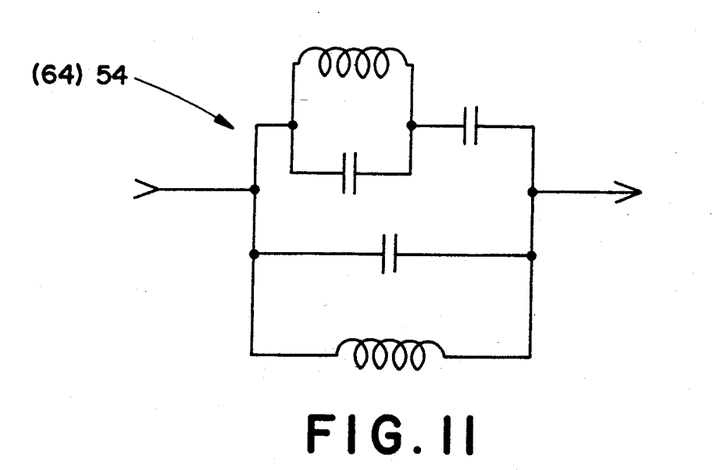

With reference to FIG. 11, the impedance array may include a combination of parallel and series resonant circuits to provide two modes of operation. The series mode provides a low impedance for the ECG signal; whereas, the parallel mode provides a high impedance at RF frequencies.

The invention has been described with reference to the preferred embodiments. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A non-invasive diagnostic apparatus comprising:
    a means for subjecting a region of interest of a patient to changing magnetic fields and radio frequency signals in order to induce and encode magnetic resonance of selected nuclei in the region of interest;
    an electrode for engaging the patient to monitor ECG signals;
    an electrically conductive lead having a clip means for selectively engaging and establishing electrical communication with the electrode, the radio frequency signals inducing radio frequency currents in the lead which currents can cause heating of the electrode;
    a temperature sensing means mounted to the clip means for sensing temperature;
    a means mounted in series between the electrically conductive lead and the electrode for passing the ECG signals while inhibiting the passage of the radio frequency currents;
    a receiving means for receiving magnetic resonance signals from the region of interest;
    a sequence control means for controlling application of magnetic field gradients and radio frequency pulses and processing the received magnetic resonance signals into diagnostic information.

2. The apparatus as set forth in claim 1 wherein the temperature sensing means is a resistive temperature device mounted in direct thermal contact with an electrically and thermally conductive portion of the clip means.

3. The apparatus as set forth in claim 1 wherein the means for passing ECG signals and inhibiting the passage of radio frequency currents includes an LC circuit having a radio frequency resonance frequency.

4. The apparatus as set forth in claim 1 wherein the means for passing ECG signals and inhibiting passage of radio frequency currents includes a resistance for attenuating the radio frequency currents.

5. A non-invasive diagnostic apparatus comprising:
    a means for subjecting a region of interest of a subject to changing magnetic fields and radio frequency signals in a preselected resonance frequency band in order to induce magnetic resonance of selected nuclei in the region of interest;

an electrode disposed adjacent the region of interest to monitor ECG signals;

an electrically conductive lead having a clip means for selective connection to the electrode, the radio frequency signals inducing radio frequency currents in the lead which cause heating of the electrode;

a filter means mounted in series with the electrically conductive lead at the clip means for blocking the passage of the radio frequency currents more than the passage of the ECG signals;

a receiving means for receiving magnetic resonance signals from the region of interest;

a sequence control means for controlling the application of magnetic field gradients and radio frequency pulses and processing received magnetic resonance signals into diagnostic information.

6. The apparatus as set forth in claim 5 wherein the filter means includes an LC circuit and a resistor connected in parallel with the LC circuit.

7. The apparatus as set forth in claim 6 further including a second LC circuit connected in series with the first LC circuit, the first and second LC circuits presenting high impedance to the resonance frequency currents.

8. The apparatus as set forth in claim 5 further including:

an analog to digital converter connected with the electrical lead for converting the signals passed along the lead to electrical digital signals;

a filter impedance means connected between the lead and the analog to digital converter for protecting the analog to digital converter from the induced radio frequency currents;

an electro-optical converter means for converting the electrical digital signals to optical digital signals and transmitting the optical digital signals along a light path.

9. A non-invasive diagnostic apparatus comprising:

a means for subjecting a region of interest of a subject to changing magnetic fields and radio frequency signals in order to induce magnetic resonance of selected nuclei in the region of interest;

an electrode for monitoring cardiac signals disposed adjacent the region of interest;

an electrically conductive lead having a clip means for selective connection to the electrode;

an impedance means mounted in series with the electrically conductive lead adjacent the clip means for inhibiting the passage of radio frequency currents and passing low frequency signals;

a temperature sensing means for sensing electrode temperature and generating an electrical temperature signal indicative thereof;

a multiplexing means for selectively connecting one of the electrical temperature and low frequency signals with an analog to digital converter, the analog to digital converter being connected with the lead to transmit digitized temperature and cardiac signals thereon;

a receiving means for receiving magnetic resonance signals from the region of interest;

a sequence control means for controlling the application of magnetic field gradients and radio frequency pulses and processing received magnetic resonance signals into diagnostic information.

10. A non-invasive diagnostic apparatus comprising:

a means for non-invasively examining an internal region of a subject in an examination region with radio frequency energy;

a monitoring means for monitoring a condition of the subject, the monitoring means including at least one electrically conductive monitor lead that extends into the examination region to a socket for selectively receiving an electrode which is mounted in contact with the subject;

a temperature sensing means for sensing a temperature at the socket.

11. The apparatus as set forth in claim 10 further including a bandpass filter means mounted closely adjacent the socket for passing monitored condition signals and blocking the passage of radio frequency currents induced in the monitor lead.

12. The apparatus as set forth in claim 10 further including a multiplexing means for selectively connecting one of the monitored condition and temperature signals to an analog to digital converter and an electrical to optical converter means for converting an output of the analog to digital converter to digital, optical signals for transmission along an optical transmission path.

13. The apparatus as set forth in claim 12 further including:

an optical signal receiving means for receiving the digital optical signals transmitted along the optical transmission path;

a sorting means for sorting bits of the received digital signal between a monitored condition signal detector and a temperature limit checking means for comparing the monitored temperature with preselected limits.

14. A non-invasive apparatus comprising:

a means for non-invasively examining an internal region of a subject in an examination region with radio frequency energy;

an electrode detachably mounted to the subject;

a monitoring means for monitoring a condition of the subject, the monitoring means including at least one electrically conductive monitor lead that extends into the examination region and is connected with the electrode;

a temperature sensing means for sensing a temperature of the electrode.

15. The apparatus as set forth in claim 14 wherein the temperature sensing means includes a temperature sensor and a temperature sensor lead extending from the temperature sensor to a temperature signal output means.

16. The apparatus as set forth in claim 15 wherein the temperature sensor is a fluoroptic sensor which generates light that changes in accordance with temperature and wherein the temperature sensor lead is an optic fiber.

17. The apparatus as set forth in claim 15 wherein the temperature sensing means is an electrical sensor and the temperature sensor lead is an electrically conductive lead and further including a filter means connected with at least one of the temperature sensor lead and the monitor lead for blocking the passage of radio frequency signals therethrough and passing low frequency signals.

18. The apparatus as set forth in claim 14 wherein the monitor lead has a socket at one end thereof, the temperature sensing means being mounted in the socket and wherein the electrode has a plug means which is releasably received in the socket.

19. The apparatus as set forth in claim 18 further including a bandpass filter means mounted closely adjacent the socket for passing monitored condition signals and blocking the passage of radio frequency currents induced in the monitor lead.

20. A method of non-invasive diagnostic examination comprising:

attaching an electrode which is connected to an electrical lead to a subject and positioning a portion of the subject to be examined in an examination region;

subjecting the examination region to changing magnetic fields and radio frequency signals in order to induce magnetic resonance of selected nuclei in the examination region, the radio frequency signals inducing radio frequency currents in the electrical lead;

monitoring a temperature of the electrode;

in response to the monitored electrode temperature exceeding preselected limits, controlling application of the radio frequency signals;

receiving magnetic resonance signals from the examination region; and, processing the received magnetic resonance signals into diagnostic information.

21. A method of non-invasive diagnostic examination comprising:

attaching an electrode which is connected by an impedance to an electrical lead to a subject and disposing a portion of the subject to be examined in an examination region;

subjecting the portion of the subject in the examination region to changing magnetic fields and radio frequency signals including a selected resonance frequency in order to induce magnetic resonance of selected nuclei of the subject, the radio frequency signals inducing radio frequency currents including the resonance frequency in the leads;

blocking passage of the radio frequency currents from the lead to the electrode while concurrently passing signals with frequencies below the selected resonance frequency from the electrode to the electrical lead;

receiving the magnetic resonance signals from the region of interest and receiving electrode signals with frequencies below the resonance frequency from the leads; and, processing the received magnetic resonance signals and electrode signals into diagnostic information.

* * * * *